United States Patent [19]

Schumann et al.

[11] 4,181,673

[45] Jan. 1, 1980

[54] PROCESS FOR PREPARING DIMETHYLHYDROGENCHLOROSILANE

[75] Inventors: Hiltraut Schumann; Christian Dathe, both of Dresden, German Democratic Rep.

[73] Assignee: VEB Chemiewerk Nunchritz, Nunchritz, Fed. Rep. of Germany

[21] Appl. No.: 5,713

[22] Filed: Jan. 23, 1979

[51] Int. Cl.² ............................ C07F 7/16; C07F 7/12
[52] U.S. Cl. ................ 260/448.2 T; 260/448.2 T
[58] Field of Search ................................ 260/448.2 T

[56] References Cited

U.S. PATENT DOCUMENTS

| | | | |
|---|---|---|---|
| 2,666,776 | 1/1954 | Nitzsche et al. | 260/448.2 T |
| 3,155,698 | 11/1964 | Nitzsche et al. | 260/448.2 T |

FOREIGN PATENT DOCUMENTS 410024  5/1974  U.S.S.R. ............................ 260/448.2 T

Primary Examiner—Paul F. Shaver
Attorney, Agent, or Firm—Tab T. Thein

[57] ABSTRACT

Single-step, pressureless process for preparing dimethylhydrogenchlorosilane (DMS=$(CH_3)_2HSiCl$) with a content of at least 97% by weight, the product being free of unsaturated hydrocarbons, by adding hexachloroplatinic acid in a catalytic amount to the first-run mixture of the direct synthesis of methylchlorosilanes, distilling between 33 and 37° C., the addition of the acid taking place before fractionation is carried out. The so obtained DMS is used for the modification of silicone products, particularly to improve specific parameters, as for instance, resistance to reversion, oil resistance and flame resistance.

9 Claims, No Drawings

PROCESS FOR PREPARING DIMETHYLHYDROGENCHLOROSILANE

The present invention relates to a single-step, pressureless process for preparing dimethylhydrogenchlorosilane (DMS $=(CH_3)_2HSiCl$) in high yield, the product being free of unsaturated hydrocarbons, and having a content of at least 97% by weight. The starting product is a first-run mixture of the direct synthesis of methylchlorosilanes, which distills between 33° and 37° C. The so obtained product is used for the modification of silicone products.

Characterization of known technical solutions of the art

It is known that in the direct synthesis of methylchlorosilanes from methylchloride and metallic silicon in the presence of copper as catalyst, $(CH_3)_2HSiCl$, DMS, is obtained as by-product. This substance is especially suitable for the modification of silicones, because it causes a considerable improvement of the parameters important in technical applications, e.g. resistance to reversion, oil and flame resistance, as well as other properties of cross-linked silicone products, e.g. silicone rubber. For that purpose, it is necessary that the DMS be of high purity, particularly free of unsaturated hydrocarbons, since otherwise the attempted modification is impaired by undesirable side reactions.

According to conventional methods, DMS was obtained from the first-run mixture of the direct synthesis distilling between 33° and 37° C. With the use of a somewhat expensive apparatus and chemical manipulations, it was possible to reach a gradual DMS increase up to 73% by weight by fractional distillation. For that purpose, the first-run mixture is treated at 10 atm and 120° C. with $AlCl_3$ for several hours, and is thereafter subjected to fractional distillation.

It is further known that DMS is supposed to be obtainable by passing hydrogen chloride into the first-run mixture in a closed system to saturation, and thereafter fractionating in an open system, the yield being a product of high purity. It is not mentioned what yields can be obtained. However, in that case, too, the use of very expensive apparatus is necessary, since the reaction has to be carried out at 3 atm excess pressure, and extensive measures have to be taken during discharge of the hydrogen chloride (provision of separators, cooling agents, etc.) in order to avoid losses of the desired volatile product, and yet the product will contain unsaturated hydrocarbons.

Thus both known processes yield DMS containing unsaturated hydrocarbons as impurities, which make the product unsuitable for the modification of special silicone products.

DMS which does not contain unsaturated hydrocarbons is obtainable on a laboratory scale by reaction of methylhydrogenchlorosilane with methylgrignard, or by reduction of dimethyldichlorosilane by splitting of methylchlorodisilanes and dimethylpolysilanes e.g. with HCl, or splitting of tetramethyldisiloxane with $CaCl_2$. The syntheses are very expensive and lead to only low yields of DMS. They are, therefore, unsuitable for technical processes.

OBJECTS OF THE INVENTION

The present invention has the object of providing a simple process, which can be carried out easily, for obtaining DMS of at least 97% by weight.

It is a further object to provide a process which yields DMS free of impurities, particularly unsaturated hydrocarbons: which starts from easily accessible products, and can be operated without pressure, in simple, inexpensive apparatus.

It is yet another object to provide a process which by use of pressure-free distillation reaches a DMS which needs no further treatment or purification operations.

Other objects and advantages of the process of the invention will become apparent from the following detailed description.

DESCRIPTION OF THE INVENTION

According to the invention, DMS containing at least 97% by weight of dimethylhydrogenchlorosilane, free of unsaturated hydrocarbons, can be obtained in high yield from the first run of the direct synthesis of methylchlorosilanes distilling between 33° and 37° C. by the addition, to the first run, of hexachloroplatinic acid as a catalyst before the fractionation takes place.

In general, two hours' refluxing of the first-run mixture with hexachloroplatinic acid is sufficient for attaining a quantitative removal of the unsaturated hydrocarbons. Subsequently, immediate distillation can be carried out for withdrawal of the product.

In order to increase the yield of DMS, it is advantageous to add other Si—H—containing compounds, especially methyldichlorohydrogensilane (MDS) to the first-run mixture.

For carrying out the process of the invention, more particularly, a first-run mixture containing at least 3% by weight DMS, preferably 25% by weight or more, is admixed with 0.01 to 0.5% by volume, preferably 0.12% by volume isopropanolic hexachloroplatinicacid solution 1.1 molar, refluxed for two hours, and immediately thereafter fractionally distilled.

In a practical embodiment, the invention considers the amount of the hexachloroplatinic acid, added to the first-run mixture, to be preferably between 0.01 and 10 grams per liter of the first-run mixture. In a further, specific modification the amount may range between 0.2 and 0.8 grams per liter of the first-run mixture.

The reaction according to the invention takes place directly in the distillation apparatus, which consists of a flask or retort, column, device for fractional distillation withdrawal, and distillate receiver.

The particular advantage of the invention consists of the effortless quantitative removal of the unsaturated hydrocarbons. Only this feature renders useful the DMS obtained by the methylchlorosilane synthesis for the modification of silicone products.

In the following, the process of the invention is described in a number of examples, but it should be understood that these are given by way of illustration and not of limitation.

For carrying out the fractionation, a column of 85 theoretical plates was used (measure of separation effectivity of a distilling column). The reflux ratio is 50:1. The DMS fraction distilling at 35° to 36° C./760 mm was at least 97% by weight and did not contain any impurities of unsaturated hydrocarbons.

| Example | Starting Mixture, amount in grams | Starting Mixture, amount of DMS in percent | Starting Mixture, addition of mos in grams | Starting Mixture, addition of a solution of hexachlorplatinic acid in ml (1.1 molar in isopropanol | DMS, yield in grams | DMS, yield in percent | DMS, purity in percent | DMS, refraction index | DMS, impurities, substance | DMS, impurities, content in percent |
|---|---|---|---|---|---|---|---|---|---|---|
| 1 | 500 | 75 | — | 0.3 | 250 | 70 | 99 | 1.3835 | a<br>b | 0.8<br>trace |
| 2 | 2500 | 25 | 375 | 3 | 510 | 79 | 97 | 1.3839 | a<br>b<br>c | 2<br>trace<br>" |
| 3 | 3700 | 25 | 500 | 3.5 | 800 | 85 | 98 | 1.3835 | a<br>c | 1.5<br>0.5 |

Impurities: $^a$methylenechloride
$^b$2-methylbutane (isopentane)
$^c$methyldichlorohydrogensilane(MSD)

What we claim is:

1. A pressureless process for preparing dimethylhydrogenchlorosilane (DMS) of the formula $(CH_3)_2HSiCl$, using as starting product a first-run mixture of a direct synthesis of methylchlorosilanes with a boiling point between 33° and 37° C., the process comprising adding to the starting product hexachloroplatinic acid as a catalyst, and subjecting the mixture to fractional distillation, thereby removing impurities otherwise not separable from the dimethylhydrogenchlorosilane.

2. The process as defined in claim 1, wherein the first-run mixture contains at least 3% by weight of dimethylhydrogenchlorosilane (DMS).

3. The process as defined in claim 1, wherein the amount of hexachloroplatinic acid added to the first-run mixture is between 0.01 and 10 grams per liter first-run mixture.

4. The process as defined in claim 3, wherein the amount of hexachloroplatinic acid is between 0.2 to 0.8 grams per liter first-run mixture.

5. The process as defined in claim 1, wherein the amount of hexachloroplatinic acid is added in an isopropanolic solution.

6. The process as defined in claim 5, wherein the isopropanolic solution is 1.1 molar, in an amount of between 0.01 and 0.5 volume % calculated on the amount of the first-run mixture.

7. The process as defined in claim 1, wherein other Si—H-containing compounds are added to the first-run mixture.

8. The process as defined in claim 7, wherein methyldichlorohydrogensilane (MDS) is added to the first-run mixture.

9. The process as defined in claim 6, wherein the amount of the isopropanolic solution is 0.12 vol. %.